(12) United States Patent
Kariathungal et al.

(10) Patent No.: US 8,553,951 B2
(45) Date of Patent: Oct. 8, 2013

(54) METHODS AND SYSTEMS FOR GROUPING RADIOLOGICAL IMAGES INTO EVENT MARKERS

(75) Inventors: Murali Kumaran Kariathungal, Hoffman Estates, IL (US); Prakash Mahesh, Hoffman Estates, IL (US); Mark M. Morita, Arlington Heights, IL (US)

(73) Assignee: General Electric Company, Schenectady, NY (US)

( * ) Notice: Subject to any disclaimer, the term of this patent is extended or adjusted under 35 U.S.C. 154(b) by 1431 days.

(21) Appl. No.: 11/755,469

(22) Filed: May 30, 2007

(65) Prior Publication Data
US 2008/0298665 A1  Dec. 4, 2008

(51) Int. Cl.
*G06K 9/00*  (2006.01)
*G06K 9/34*  (2006.01)

(52) U.S. Cl.
USPC .......................................................... 382/128

(58) Field of Classification Search
USPC ................................................. 382/128–134
See application file for complete search history.

(56) References Cited

U.S. PATENT DOCUMENTS

| | | | | |
|---|---|---|---|---|
| 6,480,732 | B1 * | 11/2002 | Tanaka et al. | 600/425 |
| 6,597,762 | B1 * | 7/2003 | Ferrant et al. | 378/62 |
| 2006/0120624 | A1 * | 6/2006 | Jojic et al. | 382/284 |
| 2010/0262605 | A1 * | 10/2010 | Mikawa | 707/740 |

* cited by examiner

*Primary Examiner* — Alex Liew
(74) *Attorney, Agent, or Firm* — Hanley, Flight and Zimmerman, LLC

(57) ABSTRACT

Certain embodiments of the present invention provide a method for radiological imaging including: viewing a study, the study including a series of radiological images interfacing with the study to allow interaction with the radiological images of the study; selecting an image from the series of radiological images to form an event marker; and grouping with the selected image at least one other neighboring image within the series of radiological images to form an event, the event ranging over a plurality of images within the series. In an embodiment, the event includes at least one of: the selected image within the series and at least one subsequent neighboring image; the selected image and at least one previous neighboring image; and the selected image, at least one previous neighboring image, and at least one subsequent neighboring image.

17 Claims, 4 Drawing Sheets

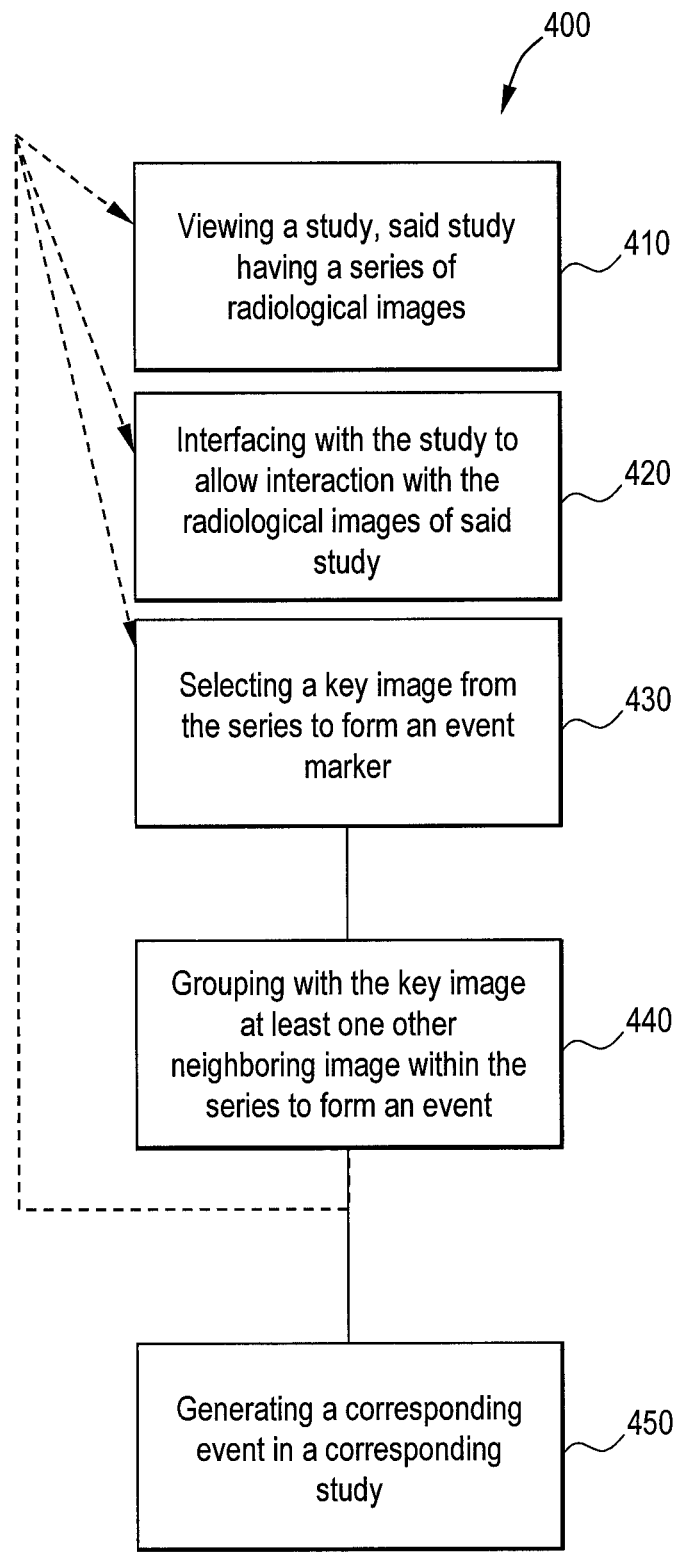

METHODS AND SYSTEMS FOR GROUPING RADIOLOGICAL IMAGES INTO EVENT MARKERS

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

Embodiments of the present application relate generally to systems and methods for radiological imaging. Particularly, certain embodiments relate to techniques for grouping radiological image data based on selected images in a study.

In radiology workflow, a clinician (e.g., radiologist) may read a study by traversing the images in the study. During this reading, some of the image(s) in the study may be of special interest to the clinician, and may be marked as significant, or key image(s). If a study contains a relatively large number of images, traversing the images to find key images may require multiple traversals.

The study may involve imaging of a patient's body part over a period of time, for example. Therefore, the images in the study may have a range of temporal positions. Within such time-based studies, certain events may be particularly clinically relevant. Some such clinically relevant events may include cardiac studies with more than one scan of the heart. Clinically relevant images can be found in one scan, and it may be helpful to link these images with other scans to facilitate diagnosis.

In some instances where there are multiple key images, which are spatially distributed in a study. During a radiology reading, a clinician may be interested in images that neighbor a key image. If the study contains multiple key images and the clinician wants to analyze the neighboring images, the clinician may wish to traverse the entire study and/or may wish to mark all the images neighboring to the key images as key images, for example. Reading workstations, such as PACS workstations, may not facilitate the capability for grouping neighboring images of key images into key image sequences, or events, for further reading.

The clinician may wish to read a study more than once. In such cases, it may be useful to mark an event for future reference. Present radiological workflow may not facilitate the clinician to group neighboring images of key images for future reading. It may be helpful, for example, to allow a user to mark events, which are significant, where these event markers may be accessed quickly for future reference. Furthermore, it may be useful to provide event markers that facilitate traversal of key images.

In an integrated volume rendering application, it may further be useful to provide event marker(s) which may be used to identify images, which belong to a volume segment. Such marker(s) may be employed to mark events in a volumetric radiological study.

In addition to marking events, a clinician may prefer to have certain image processing techniques to enhance clinical diagnosis of images in event marker(s). It also may be that clinical diagnosis of images in event markers(s) may be facilitated by a variety of image processing techniques. Thus, from one event marker to the next, it may be helpful to a clinician to apply different image processing algorithms.

Thus, there is a need for methods and systems that provide for the selection of images as event markers in a study. There is a need for methods and systems that improve the efficiency of study navigation for clinicians focusing on images which are key to the diagnostics. There is a need for methods and systems that provide event marking for volume rendering applications. Additionally, there is a need for methods and systems that provide image processing corresponding to images specified in event markers.

BRIEF SUMMARY OF THE INVENTION

Certain embodiments of the present invention provide a method for radiological imaging including: viewing a study, the study including a series of radiological images interfacing with the study to allow interaction with the radiological images of the study; selecting an image from the series of radiological images to form an event marker; and grouping with the selected image at least one other neighboring image within the series of radiological images to form an event, the event ranging over a plurality of images within the series. In an embodiment, the event includes at least one of: the selected image within the series and at least one subsequent neighboring image; the selected image and at least one previous neighboring image; and the selected image, at least one previous neighboring image, and at least one subsequent neighboring image. In an embodiment, the method further includes selecting a second image from the series of radiological images to form a second event marker; and grouping with the second selected image at least one other neighboring image within the series of radiological images to form a second event. In an embodiment, the method further includes generating from the event a corresponding event in a second study. In an embodiment, the event further includes image processing data. In an embodiment, the method further includes traversing a portion of the study based at least in part on the event. In an embodiment, the event includes a plurality of two-dimensional images. In an embodiment, the event includes a plurality of three-dimensional images.

Certain embodiments of the present invention provide a system for radiological imaging including: a viewing module for of presenting to a clinician a study including series of radiological images; an interface module for allowing the clinician to interact with the system; a selection module for selecting an image from the series of radiological images to form an event marker, wherein the event marker includes the selected image; a grouping module for grouping with the selected image at least one other neighboring image within the series of radiological images to form an event, the event ranging over a plurality of positions. In an embodiment, the event includes at least one of: the selected image and at least one subsequent neighboring image; the selected image and at least one previous neighboring image; and the selected image, at least one previous neighboring image, and at least one subsequent neighboring image. In an embodiment, the selection module is capable of selecting a second image from the series of radiological images to form a second event marker; and wherein the grouping module is capable of grouping with the second selected image at least one other neighboring image within the series of radiological images to form a second event. In an embodiment, the system further includes a generation module for generating from the event a corresponding event in a second study. In an embodiment, the event further includes image processing data. In an embodiment, event includes a plurality of two-dimensional images. In an embodiment, the event includes a plurality of three-dimensional images.

Certain embodiments of the present invention include a computer-readable storage medium including a set of instructions for a computer, the set of instructions including: a viewing routine for viewing a study, the study including a series of radiological images; a selection routine for selecting an image from the series of radiological images to form an event marker, wherein the event marker includes the selected image; and a grouping routine for grouping with the selected image at least one other neighboring image within the series of radiological images to form an event. In an embodiment, the event includes at least one of: the selected image and at least one subsequent neighboring image; the selected image and at least one previous neighboring image; and the selected image, at least one previous neighboring image, and at least one subsequent neighboring image. In an embodiment, the selection routine is capable of selecting a second image from the series of radiological images to form a second event marker; and wherein sad grouping routine is capable of grouping with the second selected image at least one other neighboring image within the series of radiological images to form a second event. In an embodiment, the set of instructions further includes a generation routine for generating from the event a corresponding event in a second study. In an embodiment, the event further includes image processing data.

BRIEF DESCRIPTION OF SEVERAL VIEWS OF THE DRAWINGS

FIG. 4 shows a flowchart for radiological imaging, according to embodiments of the present invention.

Figure 1:
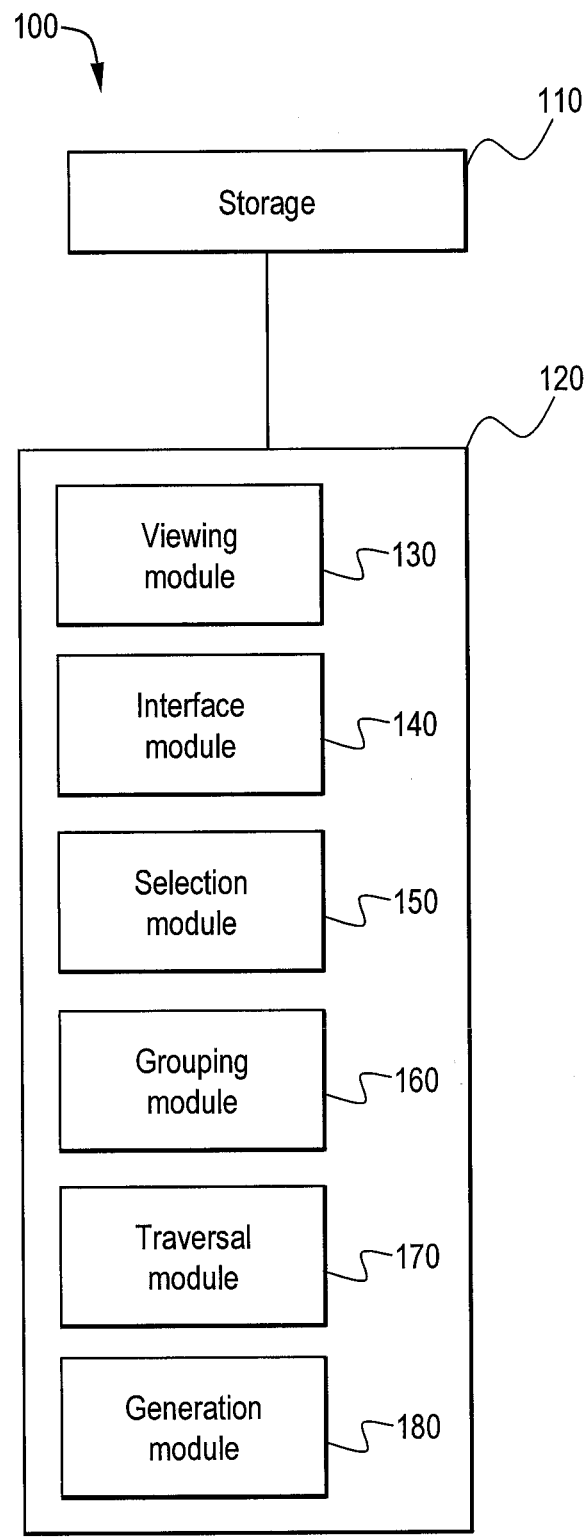
FIG. 1 shows a system for radiological imaging, according to embodiments of the present system.

The foregoing summary, as well as the following detailed description of certain embodiments of the present application, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

FIG. 1 shows a system 100 for radiological image reading, according to embodiments of the present invention. The system 100 may include a storage 110 and a processing subsystem 120. The storage 110 may be any digital storage medium, such as hard disk, optical disk, magnetic disk, RAM, ROM, flash, and/or the like, for example. The storage 110 may be capable of storing electronically a set of image data, for example. A set of image data may include radiological images, such as a radiological study, for example. A set of image data may also include associated information, such as patient identification, procedure identification, clinician identification, and/or the like, for example. The storage 110 may be integrated with processing subsystem 120, or may be physically separate. The storage 110 may communicate with the processing subsystem 120, for example, to transfer image data from the storage 110 to the processing subsystem 120.

A processing subsystem 120 may be an integrated device, such as a computer, or a collection of components. A processing subsystem 120 may be a PACS, for example. A processing subsystem 120 may interpret and execute set of instructions to run an application, routine, or subroutine, for example. The processing subsystem 120 may be capable of receiving a set of image data, for example, such as a set of image data from storage 110. A processing subsystem 120 may contain various modules, such as a viewing module 130, an interface module 140, a selection module 150, a grouping module 160, a traversal module 170, and/or a generation module 180, for example. Any given module may be a separate component that includes software and/or hardware, for example. Modules may be integrated with other modules, either completely or partially, for example. Modules may be software routines and/or applications. The modules may be capable of interaction with other modules. Modules may include a computer-readable storage medium that includes a set of instructions that facilitate the operations of the module. One or more computer-readable storage media may be storage 110 and/or may reside within processing subsystem 120, for example.

The viewing module 130 may be capable of presenting a radiological study, or a portion thereof, to a clinician. The study may include two-dimensional image data, or may include three dimensional image data (e.g. for display through a volume rendering application), for example. The viewing module 130 may receive image data from storage 100, for example. The study may include a series of images, such as radiological images, for example. The series of images (e.g. 2D or 3D images) may be over a period of time, wherein each image has a temporal position, for example. Some of the images may be clinically significant, or perceived to be clinically significant, for example.

The interface module 140 may allow the clinician to interact with the system 100. For example, the interface module 140 may receive information from the clinician through devices such as a mousing device, a keyboard, a touch screen, and/or the like. The interface module 140 may allow the clinician to interact with the study, a portion thereof, or particular images in a study, for example.

The selection module 150 may allow a clinician to select one or more key images from the series of images. For example, a clinician may determine that certain images are clinically significant (or at least perceived to be), and may then—through interface module 140—select a key image. The key image may form an event marker, for example. The event marker may, for example, include information about the temporal position of the key image. The event marker may, for example, reference a key image with associated information regarding the temporal position of the key image.

The selection module 150 may also allow a clinician to select a portion of a significant image. The selected portion may then be used in creation of an event, for example. An event, therefore, may be a series of portions of images, for example.

The grouping module 160 may group one or more neighboring images with the key image. A neighboring image may be an image proximate (within the series) to the key image, for example. However, a neighboring image need not be an adjacent image to the key image. A neighboring image may be, for example, any image within a relevant clinical period of the series of images. The grouping of images may form an event. The event may, for example, range over two or more temporal positions in the series of images, for example. An event may include the key image, and may include subsequent and/or previous neighboring images, for example.

Figure 2:
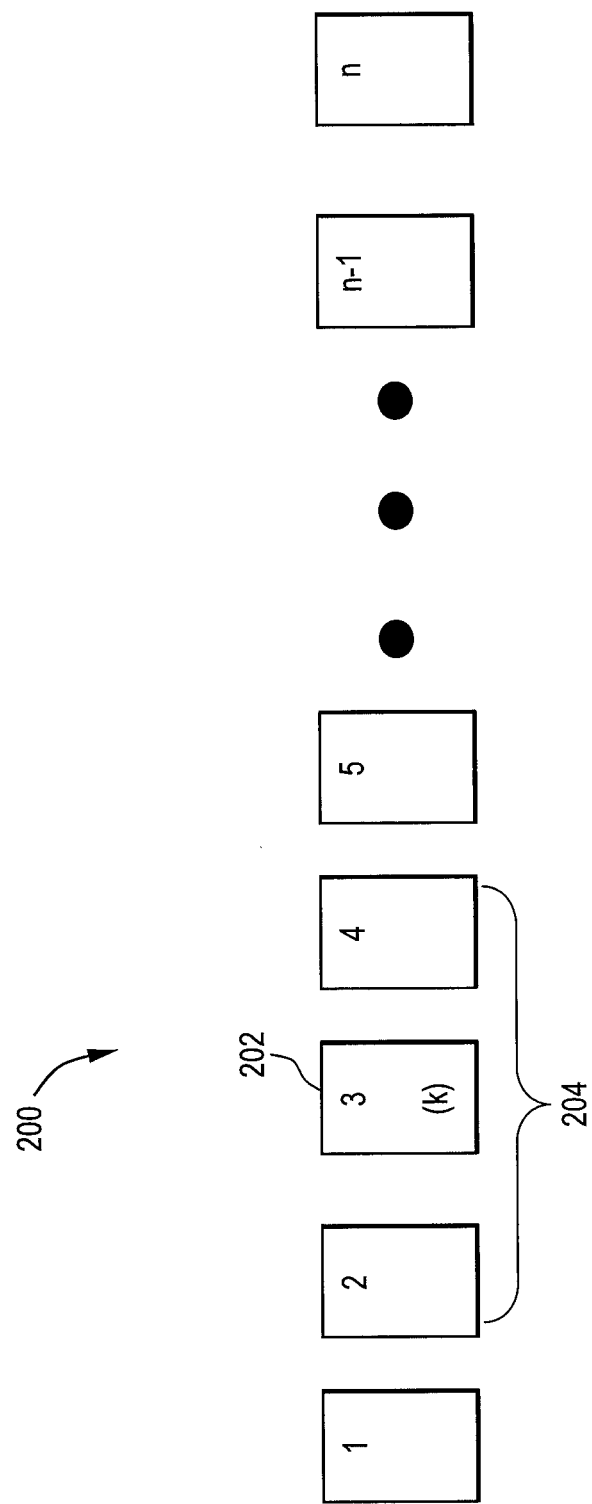
FIG. 2 shows a radiological study, according to embodiments of the present invention.

Turning for a moment to FIG. 2, an example of an event may be further illustrated. A study, or a portion thereof, 200 may include a plurality of images. The study 200 is shown to include n images. Each image has a position, such as a temporal position, for example. A clinician, when traversing the study 200 may conclude that an image—such as image 202—is a significant or key image. The clinician may then mark the significant image 202 as a key image "(k)" to form an event marker.

The clinician may then determine that it would be clinically useful to create an event including images that neighbor key image 202. For example, the user can mark an event at position k and end the event at position k+l or k−l/2 to k+l/2, where the event contains l images. An example of an event is shown as 204, including key image 202 (image 3), and neighboring images 2 and 4. In this particular example, the neighboring images are adjacent, but they need not be adjacent to be neighboring. For example, image 1 and image 5 may be neighboring image depending on the clinical time period at issue. For example, an event may include images 1-5, or may include images 1, 3, 5, or may include images 2, 3, and 5, etc.

Turning back now to FIG. 1, the traversal module 170 may facilitate traversal of a series of images. For example the traversal module 170 may facilitate selection of a key image. As another example, the traversal module 170 may facilitate selection and/or review of an event.

The generation module 180 may be able to generate a corresponding event or event marker in a corresponding study. Alternatively, the generation module may be capable of importing an event from a corresponding study into the present study at issue. In such a manner, events selected from one study may be imported/exported to a corresponding study, for example. Information about the event may be stored in association with the study in which the event was originally selected, for example. By application of the generation module 180, such event information may then be associated with the present study at issue, for example.

Image processing may be applied by one or more of the modules in processing subsystem 120. Image processing may be applicable to an image, or a series of images, such as a study or images in an event. Various image processing techniques may be available, and applicable—either automatically or by a clinician. Image processing techniques may be applied based on clinician preference, anatomy, patient, type of study, etc., for example. Image processing settings may be associated with an event, for example. This may facilitate a clinician when reviewing an event in the future, for example. By having image processing settings associated with an event, a clinician may review an event without having to reapply at least some of the image processing settings.

Some image processing techniques include applying a look-up table or window level to an image, for example. Other examples of image processing include the application of algorithm(s). For example, the image processing algorithm(s) may be capable of applying vessel analysis to show vessels, or applying bone removal analysis to remove certain bones (or portions thereof) from the images. Such techniques may be performed by application of algorithm(s) and/or filter(s), for example. One or more algorithms may be capable of enhancing and/or identifying structure in an image, or series of images, for example. An algorithm may assist and/or perform segmentation of an image or series of images, for example. By identifying various portions in an image, such identified portions may be highlighted or obscured to facilitate clinical review of a clinically significant portion, for example. An algorithm may assist in enhancement and/or identification of a patient's anatomy based on techniques other than segmentation, for example.

One or more filters may be capable of enhancing and/or identifying clinically significant portions, for example. A filter may assist and/or perform segmentation of images in the event, for example. A filter may also assist and/or perform identification of a portion that is not clinically significant in order to highlight the image portion that is significant, for example. By identifying various portions in an image, such identified portions may be highlighted or obscured to facilitate clinical review of a particular portion of the image, for example. By enhancing the clinically significant portion of an image, it may be more efficient for a clinician to analyze image data, such as a study, for example.

Figure 3:
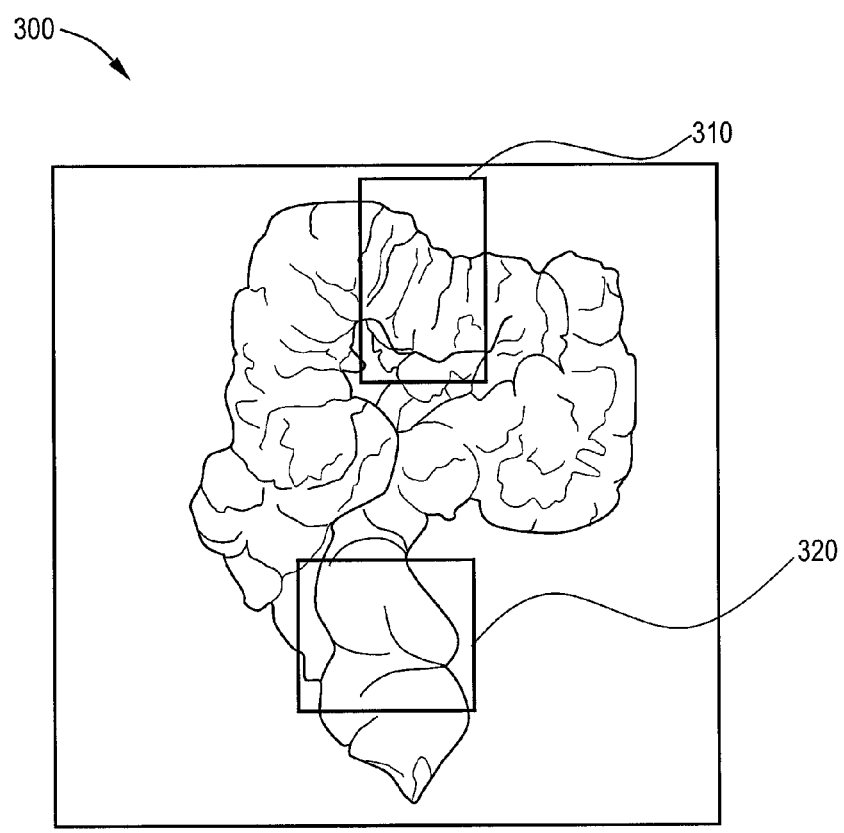
FIG. 3 shows an example of a volume rendering application, according to embodiments of the present invention.

FIG. 3 shows an example of a volume rendering application, according to embodiments of the present invention. A volumetric image 300 is shown to include a patient's colon. Using the techniques and systems described herein, a clinician may select one or more portions 310, 320 of a volumetric image as key images to form one or more corresponding event markers. Volumetric events may then be generated according to techniques and systems described herein.

FIG. 4 shows a flowchart for radiological imaging, according to embodiments of the present invention. The steps of method 400 may be performable, for example, by a PACS system, or a radiological imaging system. For example, method 400 may be performable by a system such as radiological imaging system 300, or a portion thereof. Furthermore, the steps of method 400 may be performable in a different order, or some steps may be omitted. For example, step 450 may be omitted. As another example, steps may be performed in a different order according to design and/or clinical preferences. Method 400, or a portion thereof, may be performable by one or more processing units. Method 400, or a portion thereof, may be performable by software, hardware, and/or firmware. Method 400, or a portion thereof, may also be expressible through a set of instructions stored on one of more computer-readable storage media, such as RAM, ROM, EPROM, EEPROM, optical disk, magnetic disk, magnetic tape, and/or the like.

At step 410, a series of radiological images may be viewed, such as a study, or a portion thereof. Each of the images may have a temporal position, for example. Viewing may be performable, for example, with a viewing module, such as viewing module 130. The study may include two-dimensional image data, or may include three dimensional image data (e.g. for display through a volume rendering application), for example. Image data may be stored in a storage, for example, and then displayed to a clinician.

At step 420, a clinician may interface with the study to allow interaction with the series of radiological images. Interfacing may be performed with an interface module (e.g. module 140), and may allow the clinician to interact with a radiological imaging system (e.g. system 100).

At step 430, a clinician may select a key image from the series of radiological images to form an event marker. The event marker may, for example, include information corresponding to the temporal position of the key image. A clinician may select more than one key image to form more than one event markers, for example. Selection may be performed with assistance from a selection module (e.g. module 150). Selection may be facilitated by the interfacing step 420 to allow a clinician to interact with one or more images, for example. An entire image may be selected, or a portion thereof, for example.

At step 440, one or more neighboring images may be grouped with the key image to form an event. The event may include a series of images (e.g., two or more images) spanning a plurality of temporal positions, for example. Grouping may be performable with a grouping module, such as module 160. A neighboring image may be an image proximate (within the series) to the key image, for example. However, a neighboring image need not be an adjacent image to the key image. A neighboring image may be, for example, any image within a relevant clinical period of the series of images. The grouping of images may form an event. The event may, for example, range over two or more temporal positions in the series of images, for example. An event may include the key image, and may include subsequent and/or previous neighboring images, for example. Grouping may be performable through clinician directive, clinician preference, patient, anatomy, procedure, and/or the like. Steps 430 and 440 may be repeated to generate additional events according to clinician preference, for example. As discussed above, steps may be performed in sequence, parallel, and/or the like, for example.

At step 450, a corresponding event may be generated in a corresponding study. The generation may be performed by a generation module, such as module 180. Generation may be based on an entire event, for example. Generation may be performed by exporting an event from the original study to a corresponding study, for example. Generation may be performed by importing an event from an original study into a corresponding study, for example.

As an illustrative example, method 400 may be performed in the following manner. At step 410, a clinician views a volumetric study of a patient's colon on a PACS workstation. At step 420, the clinician interfaces with the study with a mousing device. At step 430, the clinician selects, with the mouse, an envelope portion of the patient's colon. The selection is performed on an image with a significant temporal position, and is marked as a key image. The key image forms an event marker. At step 440, a series of neighboring images—previous to and subsequent to the key image—are grouped into an event. The grouped images correspond to the envelope portion selected at step 430. Steps 410 are then repeated to select a second event corresponding to a different portion of the colon, and over the same temporal positions of the first event. The clinician performs image processing to adjust the window level and look up table of the images in the event. The image processing parameters are then associated with the event. At step 450, during a later-performed study of the same patient's colon, the events are imported to the later-performed study along with the image processing information. The clinician can then quickly navigate the second study to compare images from the events in the first study.

In an embodiment, system 100 includes a computer-readable medium, such as a hard disk, floppy disk, CD, CD-ROM, DVD, compact storage, flash memory and/or other memory. The medium may be in storage 110, or subsystem 120. The medium may include a set of instructions capable of execution by a computer or other processor. The functions in flowchart 400 described above may be implemented, at least in part, as instructions on the computer-readable medium.

For example, the set of instructions may include a viewing routine for viewing a study including a series of images, the images having a temporal position. The viewing routine may facilitate implementation of step 410, described above in conjunction with method 400. The viewing routine may facilitate other aspects of system 100 and method 400 described above, for example.

Additionally, the set of instructions may include a selection routine for selecting a key image from the series of images to form an event marker. The event marker may include information corresponding to the temporal position of the key image. The selection routine may be able to facilitate implementation of step 430 or other steps, for example. The selection routine may be included in selection module 150.

Additionally, the set of instructions may include a grouping routine for grouping at least one neighboring image with the key image. The grouping routine may be able to facilitate implementation of step 440 or other steps, for example. The grouping routine may be included in grouping module 160, for example.

Additionally, the set of instructions may include a generation routine for generating a corresponding event in a corresponding study from the event. The generation routine may be able to facilitate implementation of step 450 or other steps, for example. The grouping routine may be included in generation module 180, for example.

Furthermore, the set of instructions may include image processing routines or that automatically or manually process image data. Image processing may be performable as described herein.

Thus, embodiments of the present invention provide methods and systems for the selection of events in a study. Embodiments of the present invention provide methods and systems for improving the efficiency of study navigation for clinicians focusing on key images, which are part of events. Embodiments of the present invention provide methods and systems for event marking for volume rendering applications. Additionally, embodiments of the present invention provide methods and systems for image processing corresponding to events.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. For example, features may be implemented with software, hardware, or a mix thereof. Therefore, it is intended that the invention not be limited to the particular embodiment disclosed, but that the invention will include all embodiments falling within the scope of the appended claims.

The invention claimed is:

1. A method for radiological imaging, the method comprising:
    presenting a first study including a series of radiological images;
    allowing an interaction with said radiological images of the first study, wherein the interaction includes:
        selecting a first image from the first study to form an event marker; and
        grouping, with the first image, at least one other neighboring image within the first study to form a first event ranging over a plurality of images within the first study; and
    generating a second event in a second study corresponding to the first event;
    wherein a range of temporal positions of the second event corresponds to a range of temporal positions of the first event.

2. The method of claim 1, wherein the first event in the first study comprises at least one of: the first image within the series and at least one subsequent neighboring image; the first image and at least one previous neighboring image; or the first image, at least one previous neighboring image, and at least one subsequent neighboring image.

3. The method of claim 1 further comprising:
    selecting a second image from the first study to form a subsequent event marker; and
    grouping, with the second image, at least one other neighboring image within the first study to form a subsequent event in the first study.

4. The method of claim 1, wherein the first event in the first study further comprises image processing data.

5. The method of claim 1 further comprising traversing a portion of the study based at least in part on the first event in the first study.

6. The method of claim 1, wherein the first event in the first study comprises a plurality of two-dimensional images.

7. The method of claim 1, wherein the first event in the first study comprises a plurality of three-dimensional images.

8. A system for radiological imaging comprising:
   a viewing module configured to present to a clinician a first study comprising series of radiological images;
   an interface module configured to allow the clinician to interact with the system;
   a selection module configured to select a first image from the first study to form an event marker including the first image;
   a grouping module configured to group, with the first image, at least one other neighboring image within the first study to form a first event ranging over a plurality of positions; and
   a generation module configured to generate a second event in a second study corresponding to the first event, wherein a range of temporal positions of the second event corresponds to a range of temporal positions of the first event.

9. The system of claim 8, wherein the first event in the first study comprises at least one of: the first image and at least one subsequent neighboring image; the first image and at least one previous neighboring image; or the first image, at least one previous neighboring image, and at least one subsequent neighboring image.

10. The system of claim 8, wherein the selection module is further configured to select a second image from the first study to form a subsequent event marker; and
   wherein the grouping module is further configured to group, with the second image, at least one other neighboring image within the first study to form a subsequent event in the first study.

11. The system of claim 8, wherein the first event further comprises image processing data.

12. The system of claim 8, wherein the first event comprises a plurality of two-dimensional images.

13. The system of claim 8, wherein the first event comprises a plurality of three-dimensional images.

14. A tangible computer-readable storage device or storage disc including a set of instructions for a computer, the set of instructions comprising:
   a viewing routine for viewing a first study comprising a series of radiological images;
   a selection routine for selecting a first image from the first study to form an event marker including the first image;
   a grouping routine for grouping, with the first image, at least one other neighboring image within the first study to form first event; and
   a generation routine for generating from the first event a corresponding second event, wherein a range of temporal positions of the second event corresponds to a range of temporal positions of the first event.

15. The storage device or storage disc of claim 14, wherein the first event in the first study comprises at least one of: the first image and at least one subsequent neighboring image; the first image and at least one previous neighboring image; or the first image, at least one previous neighboring image, and at least one subsequent neighboring image.

16. The storage device or storage disc of claim 14, wherein the selection routine is capable of selecting a second image from the first study to form a subsequent event marker; and
   wherein the grouping routine is capable of grouping, with the second image, at least one other neighboring image within the first study to form a subsequent event in the first study.

17. The storage device or storage disc of claim 14, wherein the first event in the first study further comprises image processing data.

\* \* \* \* \*